(12) United States Patent
Possover

(10) Patent No.: US 9,314,629 B2
(45) Date of Patent: Apr. 19, 2016

(54) METHOD FOR RECOVERING BODY FUNCTIONS

(71) Applicant: Marc Possover, Hagendorn (CH)

(72) Inventor: Marc Possover, Hagendorn (CH)

(\*) Notice: Subject to any disclaimer, the term of this patent is extended or adjusted under 35 U.S.C. 154(b) by 17 days.

(21) Appl. No.: 13/650,161

(22) Filed: Oct. 12, 2012

(65) Prior Publication Data

US 2013/0096640 A1 Apr. 18, 2013

Related U.S. Application Data

(60) Provisional application No. 61/546,575, filed on Oct. 13, 2011.

(51) Int. Cl.
*A61N 1/00* (2006.01)
*A61N 1/36* (2006.01)
*A61N 1/05* (2006.01)

(52) U.S. Cl.
CPC ........ *A61N 1/36103* (2013.01); *A61N 1/36057* (2013.01); *A61N 1/0551* (2013.01); *A61N 1/36003* (2013.01); *A61N 1/36025* (2013.01); *A61N 1/36071* (2013.01); *A61N 1/36082* (2013.01); *A61N 1/36146* (2013.01)

(58) Field of Classification Search
CPC .......... A61N 1/36071; A61N 1/36003; A61N 1/0551; A61N 1/36025; A61N 1/36082
USPC ....................................... 607/39–41
See application file for complete search history.

(56) References Cited

U.S. PATENT DOCUMENTS

| | | | |
|---|---|---|---|
| 3,650,276 A * | 3/1972 | Burghele et al. | 607/27 |
| 2004/0073270 A1 * | 4/2004 | Firlik et al. | 607/48 |
| 2005/0021106 A1 * | 1/2005 | Firlik et al. | 607/45 |
| 2007/0100387 A1 * | 5/2007 | Gerber | 607/41 |
| 2007/0198065 A1 * | 8/2007 | Possover | 607/40 |
| 2010/0174340 A1 * | 7/2010 | Simon | 607/40 |

\* cited by examiner

*Primary Examiner* — Niketa Patel
*Assistant Examiner* — Lindsey G Hankins
(74) *Attorney, Agent, or Firm* — Bachman & LaPointe, PC

(57) ABSTRACT

A method for treating an impaired body function in a patient, including the steps of (a) laparoscopically implanting at least one neuroprothesis electrode on a least one endopelvic nerve root of a patient; (b) electrostimulating the nerve root with the electrode for a predetermined time period to induce a body function of the patient; and (c) during the predetermined time period, instructing the patient to mentally concentrate on performing the body function.

7 Claims, 1 Drawing Sheet

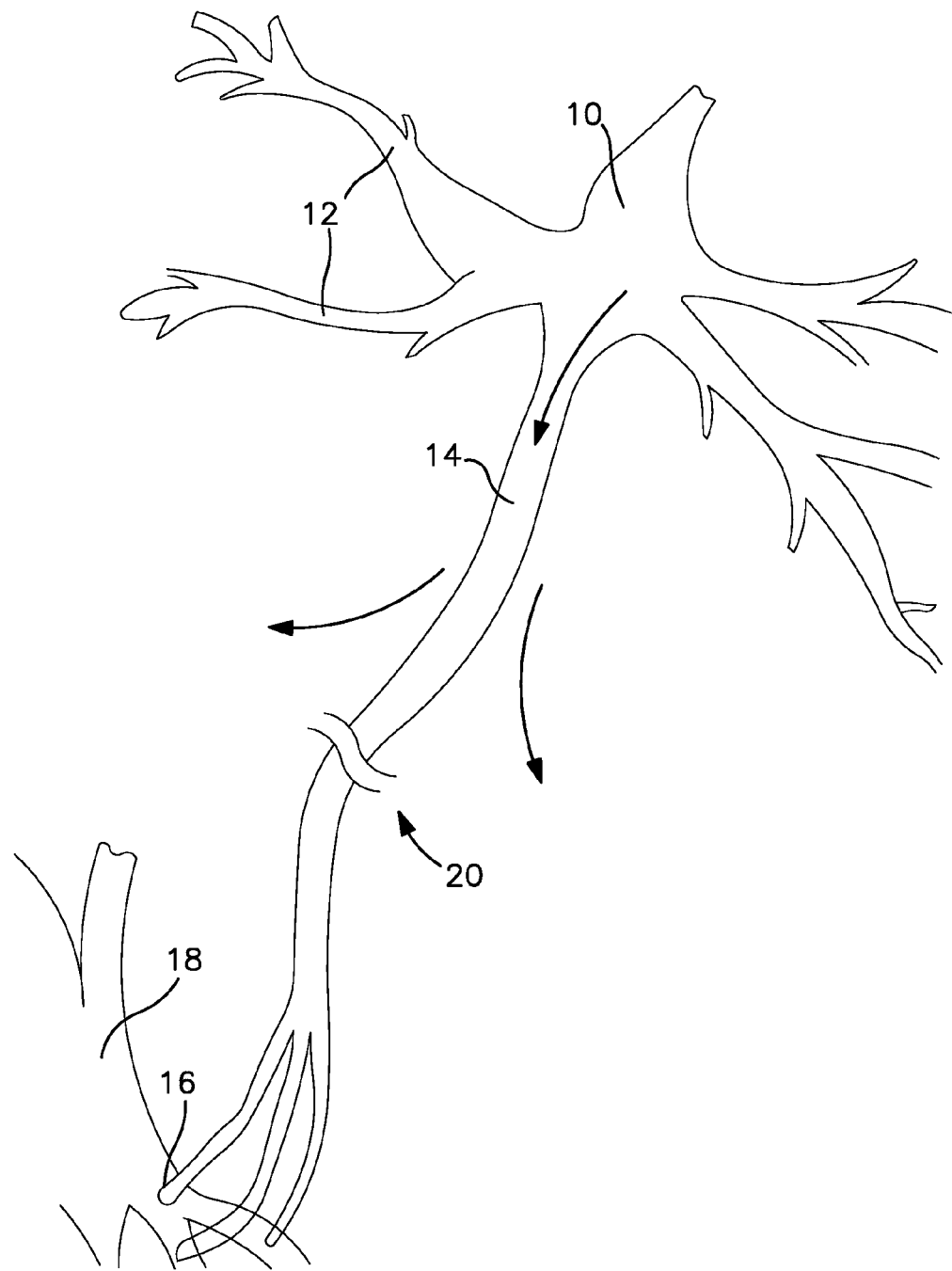

METHOD FOR RECOVERING BODY FUNCTIONS

CROSS REFERENCE TO RELATED APPLICATIONS

This application claims the benefit of provisional patent application No. 61/546,575 filed Oct. 13, 2011.

The invention relates to treatment of patients with at least partial loss of body functions, and more particularly to treatment of patients who have suffered spinal cord injuries and other pathologies which interfere with communication between the brain and nerve roots which are responsible for the body function.

Spinal cord injuries and other pathologies such as spina bifida, spinal cord tumors, cauda equine and the like can partially or completely remove supraspinal input to lumbosacral spinal circuits, and lead to permanent, complete or partial paralysis of legs, pelvic organs (bladder/intestinal/sexual) and also loss of sensation and equilibrium.

Numerous treatments and strategies for treatment for spinal cord injury and pathology seek to maximize recovery of the loss of body functions impacted in this manner.

Spinal cord injuries and pathologies can destroy axons, but the neurons to which they belong often are spared. Neurons simply do not regenerate and send out new axons, however, and several strategies have been developed to attempt to cause axon re-growth and remyelinisation. The invention is directed to a method of addressing this need.

SUMMARY OF THE INVENTION

The present inventor has realized that in order to rebuild nerve circuitry and lost function, newborn axons must travel distances of up to several feet, and must also recognize their target neurons in order to form working connections. According to the invention, a method has been developed which enhances the ability for these connections to form after injury which has disrupted them.

According to the invention a method is provided for treating an impaired body function in a patient, comprising the steps of (a) laparoscopically implanting at least one neuroprothesis electrode on at least one endopelvic nerve root of a patient; (b) electrostimulating the nerve root with the electrode for a predetermined time period to induce a body function of the patient; and (c) during the predetermined time period, instructing the patient to mentally concentrate on performing the body function.

It is believed that when following the method of the present invention, focusing on the desired body function helps send a signal or otherwise energize the receiving end of signals from the axon and, thus, helps axons find the proper neuron to which communication is needed.

BRIEF DESCRIPTION OF THE DRAWINGS

A detailed description of preferred embodiments follows, with reference to the attached drawings, wherein:

FIG. 1 schematically illustrates a method according to the invention.

DETAILED DESCRIPTION

The invention relates to a method for treating an impaired body function in a patient. More specifically, the invention relates to a method for re-establishing communication between a nerve root and the brain of a patient after this communication has been interrupted by a spinal cord injury or the like. FIG. 1 schematically illustrates a neuron 10 with various dendrites 12 and an axon 14 which extends from neuron 10 and eventually connects with receptors 16 for example of other neurons 18. Electrical impulses are carried by axon 14 in the normal and proper operation of the central nervous system. An injury schematically illustrated at 20 can serve to interrupt the delivery of electrical impulses from axon 14 to its receptor 16, and solving this problem is a goal of the present invention.

As discussed herein, it is known that certain therapies can serve to regenerate and cause growth of axon 14. However, this growth is not directed, and is not useful unless the growth reconnects to the desired receptor 16 to allow proper communication. This communication on a larger scale beyond that illustrated in FIG. 1 is properly described as being between a patient's brain and nerves which cause a particular body function. According to the invention, a patient is treated through electrostimulation of a nerve related to a lost body function while simultaneously directing the patient to concentrate or focus on that desired function, and it is believed that this combination of steps causes axon re-growth toward the desired receptor.

The present invention is based on the trans- or retroperitoneal laproscopic (endoscopic, LESS, NOTES . . . ) implantation of neuroprothesis to the endopelveo-abdominal nerves such as the sciatic nerve, femoral nerve, obturator nerve, iliac nerve, sacral plexus, sympathetic (hypogastric plexuses, sympathetic trunks) and parasympathetic nerves and plexuses (pelvic splanchnic nerves).

Current developments of video endoscopy and microsurgical instruments enables unique access to all pelvic nerves and plexuses, providing visibility with magnification of the structures and the possibility to work with appropriate instruments. (Possover M. *Journal Gynecological Surgery-Endoscopy, Imaging, and Allied Techchiques* 2004; 1: 87-90 Possover M et al. *Min Invas Ther & Allied Technol* 2004; 13: 362-376—Possover M et al. *Surg Lap Endosc Percutan Tech* 2007; 17; 508-510).

Laparoscopic trans- or retroperitoneal approach is the only technique that enables selective placements of electrodes to all pelvic nerves and plexuses. This technique, also called "Laparoscopic Implantation Of Neuroprothesis", or "LION procedure" permits the selective placement of multiple channel electrodes to all pelvic nerves and plexuses which enable multiple strategies of neuromodulation for control of different pelvic pains and/or dysfunctions at the same time (Possover M *Neuromodulation* 2010; 13: 141-144).

This evolution also presents new therapeutic options in the management of patients suffering from: neurogenic pathologies of the peripheral (multiple sclerosis, polyneuropathis, neuromas and the like) and of the central (multiple sclerosis, Parkinson syndromes, stroke and the like) nervous systems, as well as patients with spinal cord injuries.

The LION procedure enables implantation of electrodes to the different pelvic nerves involved in pelvic functions and locomotion. Thus, pelvic nerve stimulation allows for control of spasticity in the lower extremities by muscle training, allowing for electrical induced skin blood flow improvement; optimal prophylaxis against decubitus lesions (Possover M et al *Neurourology and Urodynamics* 2010); blockade of the knees in extension by femoral stimulation with stabilization of the pelvis by concomitant sciatic stimulation which enables lower paraplegics (<Th7) to recover an automatic alternative locomotion; and for "standing up" by tetraplegics.

In children with spina bifida, the LION procedure offers a unique method for controlling pelvic floor dysfunction using selective pelvic nerve stimulation and bypassing the points of anatomic abnormalities and scar tissue due to previous dorsal surgeries. Laparoscopic Neuro-Navigation (Possover M et al. *Min Invas Ther & Allied Technol* 2004; 13: 362-367) is an essential technique in this pathology since it grants an exact functional exploration and cartography of the pelvic nerves allowing for a more selective stimulation adapted to specific nerve damages.

Electrical stimulation transmitted to the nerves is accomplished by a pacemaker, wherein permanent, continuous, or sequential stimulation is created without requiring the patient's attention or participation. Hence: (a) Sciatic stimulation reduces spasticity in the lower extremities by muscle training and/or stimulating sciatic afferent fibers that induce development of leg muscle growth. Particular training of gluteal muscles in combination with increasing blood flow of the skin and vascularisation (by stimulating vegetative fibers contained in the sciatic nerve itself, involved in the vascular system of the lower limbs), protects the patient from developing decubitus lesions and osteoporosis (contraction of muscle, inducing traction to the ligaments connected to the muscle thereby inducing pressure on the bones) (b) Further, femoral and obturator stimulation has the same effects in their own muscles and skin components. (c) Stimulation of lower limb nerves increases systemic blood pressure as seen in paraplegics with lesions above Th4 as well as tetraplegics who suffer from hyponia. Thus, this stimulation helps to avoid hypertensive crises (dystonia). (d) Stimulation of pelvic nerves involved in innervations of pelvic visceral organs control dysfunctions, such as bladder and intestinal hyperactivity, as well as dyssynergia and spasticity of the pelvic floor.

Selective stimulation of pelvic nerves as reported by previous patents, permits the recovery of bladder and intestinal voiding functions, standing up, standing and locomotion by stabilization of the pelvis (stimulation of the sciatic nerves and/or its branches, the gluteal nerves and the iliac nerves) as well as the control of extension/flexion of the knee (stimulation of femoral nerves).

Standing up, in combination with gluteal muscle training and increased blood flow (discussed above) protects a patient from decubitus lesions, especially in the buttock. Also, inducing pressure to the bones is an optimal prophylaxis against osteoporosis and thrombosis in the lower extremities. This is part of rehabilitation therapy which helps to maintain bone and muscle mass, and is vital for the general health of people with spinal cord injuries.

Three spinal cord injury cases are discussed herein. Two of these cases are tetraplegic ASIA A and one is incomplete Th10 ASIA B. All three had undergone a LION procedure to pelvic nerves for recovering bladder/intestinal function and locomotion (the Th10). Additionally, one patient was further affected by a postsurgical incomplete cauda equine. He had also undergone a LION procedure to the sacral plexus for recovering bladder voiding. In this case, a sacral plexus stimulation enabled a micturition with residual <100 ml after a period of bladder training of one month.

One year later, the patients recovered normal spontaneous and voluntary micturition with normal residuals (<10 mil), recovery of spontaneous erection and partial recovery of sensitivity in several sacral dermatomes without further need of stimulation. The incomplete Th10 patients presented preoperative bladder retention with bladder overactivity treated with anticholinergics. These patients suffered complete loss of erection as well as loss of motion and sensation in the left leg.

The LION procedure had first permitted an electrical-controlled recovery of bladder and intestinal functions and recovery of extension of the left knee (femoral nerve stimulation) enabling the patient's locomotion with a walker.

Four months later, the patient presented recovery of sensation in lumbal dermatomes L1-4 and recovery of voluntary extension of the left knee without any stimulation (muscle force 3/10).

Six months later, the patient further stimulated the nerves, and also recovered motion of the toes (sacral dermatomes) obviously due to axon re-growth and such a control on extension and stabilization of the left knee (without stimulation) that the patient is now able to walk on both legs with the use of crutches.

The two tetrapelegics reported partial recovery of sensation in the lumbosacral dermatomes and motion in their toes.

These findings show that electrostimulation of pelveo-abdominal nerves seems to induce regeneration or reconnection and/or guidance for spinal axons aiding the proper reconnection to lower motor neurons below the spinal cord injury, for recovery of sensations and functions in both complete and partial spinal injuries. Electrical stimulation/modulation of pelvic nerves is believed to induce retrograde information to high levels of the central nervous system, enabling axonal regeneration with proper connection supported according to the invention. This permits recovery of voluntary, controllable and harmonious motion, physiological bladder, intestinal and sexual functions, superficial and profound sensitivities, and equilibrium.

According to the inventor, concomitant "thinking" about the physiological function by the patient, induced simultaneously with electrical stimulation, is believed to help guide axons to their proper distal nerves and therefore, be a way to cure or repair spinal cord injury.

This therapy could be combined with other pharmaceutical, systematic or local treatments and training, and may additionally be combined with stem cell or olfactive cell treatments. Such therapy could provide treatment and cure for spinal cord injuries and pathologies, as well as spina bifida, cauda equine, multiple sclerosis and other neurogenic pathologies of the central nervous system.

Further treatments, according to the invention, could involve treating and inhibiting of spinal cord fibrosis, with treatments for axonal regeneration/growth and peripheral pelvic nerve stimulation. Stimulation of pelvic nerve could also permit transformation of non-functional spinal circuits into functional states after the loss of brain input.

Further testing according to the invention was conducted in a tertiary referral advanced laparoscopic gynaecology and neuropleveologic setting.

Two incomplete spinal cord injured patients underwent a laparoscopic implantation of electrodes to the pelvic nerves for recovery of lost functions. The first patient was suffering from an incomplete cauda equine with bladder retention and loss of sensation in major sacral dermatomes. The second patient, having an incomplete Th10 lesion, was suffering from bladder overactivity with a sphincter-detrusor-dyssynergia, from spasticities in both lower extremities as well as a complete loss of sensation and motion from the left leg.

In both cases, postoperative pelvic nerve stimulation enabled patient recovery through means of electrical-induced bladder control and knee extension. These treatments were conducted with simultaneous direction to the patient to focus on the stimulated body function, and each patient has presented, over a period of months following their treatment, a successful recovery of functions, even without stimulation.

Thus pelvic nerve stimulation seems to influence axon re-growth and proper mental support to help guide proper reconnection in spinal cord-injured patients.

Adult spinal cord injury dramatically changes the life of the affected person. This includes the loss of skeletal muscle control, sensations below the injury, and serious disturbances to the autonomic nervous system.

These symptoms combine, often producing a profound deterioration in the quality of life due to loss of autonomy.

Adult spinal cord injury often leads to permanent functional deficits because the regeneration of injured axon and the reorganization of the remaining circuitry are insufficient in the human central nervous system.

Contrary to the long held clinical belief that adult CNS, once injured, does not possess any regenerative ability, advances in neuro science have show that a mature CNS has a limited ability to regenerate after injury. Research is ongoing in this field. In order for successful regeneration to occur, a series of biological events must take place. A key component of spinal cord repair requires stimulation to regenerate axons, but that does not appear to be enough for functional recovery. Newborn axons must also travel distances up to several feet and forge working connections and re-establish functioning synapses. Recognition of their target neurons and coordination by central control is essential to promote harmonic, controlled and voluntary functions, avoiding skeletal muscle and organ spasticities. Several experimental strategies have been tested to activate locomotor circuits in mammals after a complete spinal cord transaction, including pharmacological treatments. (Chau C et al. *J Neurophysio* 1998; 79: 392-409—Antri et al. *Eutr J Neurosci* 2003; 18: 1963-1972—Landry E S et al. *Eur J Neurosci* 2006; 24: 535-546), epidural (Ichiyama R M et al. *J Neurosci* 2008; 28: 7370-7375—Ischiyama R M et al. *Neurosci Lett* 2005; 383: 339-344—Gerasimenko Y P et al. *J Neurophysol* 2007; 98: 2525-2536) or intraspinal (Guevremmont L et al *IEEE Trans Neural Syst Rehabil Eng* 2006; 14: 266-272—Barthelemy D et al. *J Neurophysiol* 97: 1986-2000) electrical stimulation, and motor triaining (Kubasak M D et al. *Brain* 2008; 131: 264-276—Ichiyama R M et al. *J Neurosci* 2008: 28: 7370-7375—Chau C et al *J Neurophysio* 1998; 79: 392-409—De Leon R D et al *J Neurophysiol* 199; 81: 85-94—Tillakarantne N J et al. *J Neurosci* 2002; 22: 3130-3143). Epidural electrical stimulation applied dorsally at the lumbar L2 (Ichiyama R M et a. *J Neurosci* 2008; 28: 7370-7375—Ischiyama R M et al. *Neurosci Lett* 2005; 383: 339-344) or sacral S1 (Gerasimenko Y P et al. *J Neurophysiol* 2007; 98: 2525-2536—Lavrov I et al. *J Neurosci* 2008; 6022-6029) Spinal segments induce rhythmic hindlimb movements. Locomotor training, notably in conjunction with pharmacological or electrical stimulation (Ichiyama R M et al. *J Neurosci* 2008; 28 7370-7375) interventions, can promote use-dependent plastic changes in sensorimotor circuits below the injury (Tillakarantne N J et al. *J Neurosci* 2002; 22: 3130-3143—Petruska J C et al. *J Neurosci* 2007; 27: 4461-4471—Cote M P et al. *J Neurosci* 2004; 24: 11317-11327) that lead to specific improvements of stepping patterns. Peripheral nerve transplants also have shown promise as a way to patch nerve circuits. It is doubtful that a single researched element will provide the ultimate cure of spinal cord regeneration. However, shared evidence from many research trials may point the way toward figuring out ultimately what needs to be done. Here we report about two incomplete spinal cord injured persons who had undergone a laparoscopic implantation of neural electrodes to the pelvic nerves primary for electrical-induced recovery of functions, and conclude that one important advance is possible through simultaneous electrostimulation and patient mental focus on a lost body function.

Depending upon the condition of the patient, and particularly when treatment involves attempting to restore impaired muscle movement, the frequency charge modulation of the electrostimulating step can advantageously be conducted at low or high frequencies. For treating of an impaired body function involving muscle movement, a high frequency charge modulation is preferred and this high frequency is preferably at least 10 kHz and greater, typically up to 50 or 60 kHz. On the other hand, the broad scope of the present invention can be applied to a patient who may be comatose, and under these circumstances, a low frequency charge modulation is preferred, typically at a frequency of up to 10 Hz.

Patient X, presented with partial cauda equine after a spinal surgery for discus hernia. He was suffering from a bladder retention managed by self-catheterization, chronic constipation and loss of erection. Neurologic examination yielded objective loss of sensation in all sacral dermatomes except in the dermatomes S2 and S3 on the right side with a rest of sensation estimated by the patient at 3/10. Urodynamic testing confirmed a detrusor hypotonia with pressures not exceeding 20 cm $H_2O$. The patient was highly motivated and asked for procedures that could improve his bladder function. We performed a laparoscopic implantation of a quadripolar electrode to the right sacral plexus according to the technique previously recorded (Possover M (2010)) *The laparoscopic implantation of neuroprothesis to the sacral plexus for therapy of neurogenic bladder dysfunctions after failure of percutaneous sacral nerve stimulation. Neuromodulation* 13: 141-1444).

The second patient was suffering from an incomplete spinal cord injury Th10. He presented a bladder over activity with a sphincter-detrusor-dysynergy that obliges him to self-catherization. Locomotion was possible by preservation of partial motion of the right leg and knee-orthesis left. Pelvic organs dysfunction was confirmed by urodynamic testing while neurologic examination show a complete loss of motion and sensation in the left leg. A LION procedure to both sciatic nerves and pudendus nerves for controlling pelvic organs was performed. A third electrode was placed to the left femoral nerve for recovery of electrical induced knee extension for locomotion without orthesis.

In both patients, no pre- or postoperative complication occurred.

In the first patient, spontaneous micturition with residual surrounding 100 ml could be obtained during the test-phase, so that a permanent generator was implanted. At four months follow-up, urodynamic testing showed a micturition under sacral neuromodulation (300 us/30 Hz/1.2V) with physiologic parameters and residual<50 ml.

At one-year follow-up, there was no change.

Several research studies conducted on comparative SCI regeneration in other species, have established that a variable degree of functional recovery is possible even when synaptic connections are inappropriate, and some behavioral recovery is possible (Wood M R, Cohen M J. *Synaptic regeneration and glial reactions in the transected spinal cord of the lamprey. J Neurocytol.* 1981; 10(1): 57-79). While basic scientists strive to develop strategies to restore neurological connections between the brain and body of spinal cord injured persons, bioengineers are working to restore functional connections via advanced computer modeling systems and neural prostheses. Another concept for use of electrical stimulation in spinal cord injured peoples is to promote peripheral nerve regeneration in a desired direction using stimulation around the damaged spinal cord. Frequency of stimulation is then an important factor in the success of both quality and quantity of axon regeneration as well as growth of the surrounding myelin and blood vessels that support the axon. Various researchers studying the effects of weakly applied electric fields on the innately regenerating axons have a role to play in facilitating axonal regeneration, possibly by providing neurotropic guidance to the growing axons (Borgens R B, Bohnert D M. *The responses of mammalian spinal axons to an applied DC voltage gradient.* (*Exp Neurol.* 1997; 145: 376-389—McCaig C D, Erskine L.) nerve growth and nerve guidance in a physiological electrical field. (In: McCaig C D, editor. *Nerve growth and guidance.* London: Portland Press Ltc. 1996. pp. 151-170—McCaig C D, Sangster L, Stewart R. *Neurotrophins enhance electric field-directed growth cone guidance and directed nerve branching. Dev Dyn.* 200; 217: 299-308—Patel M, Poo M-M. *Orientation of neurite growth by extracellular electric fields. J Neuro Sci* 1982; 2: 483-496).

In vitro experiments have demonstrated that a DC electric field can induce nerve growth and that nerve fibers orient themselves parallel with the long axis of the voltage gradient (Jaffe L F, Poo M-M. *Neurites grow faster towards the cathode than the anode in a steady field. J Exp Zool.* 1979; 209: 115-127). Borgens et al. demonstrated in animal studies that regenerated axons with applied DC fields were also able to make functional synaptic connections with the caudal end of the injured spinal cord when the cathode electrode was placed caudal to the spinal cord injury. In contrast, when the cathode electrode was place rostral to the injury, only sensoric axon recovery developed (Borgens R B, Blight A R, McGinnis M E R. *Functional recovery after spinal cord hemi section in guinea pigs: the effects of applied electric fields. J Comp Neurol.* 1990; 296(4): 634-653). Other experimental studies also indicated that electrical stimulation can lead to significant functional recovery but not due to a true regeneration, but more to alternate synaptic pathways (Wallace M C, Tator C H, Piper L *Recovery of spinal cord function induced by direct stimulation of the injured rat spinal cord.* (*Neurosurg.* 1987; 20(6): 878-884).

All this research has increased current knowledge in neuroscience. However, significantly-increased therapeutic approaches have not been demonstrated until now, even in human experiments (Shapiro S. Borgens R B, Pascuzzi R, et al.). *Oscillating field stimulation for complete spinal cord injury in humans: a phase 1 trial J. Neurosurg Spine* 2005; 2:3-10).

The present application of neuromodulations is not based on application of an electrical field to the damaged spinal cord, but on the implantation of electrodes to the major pelvic nerves the laparoscopic way. (Possover M (2010). *The laparoscopic implantation of neuroprothesis to the sacral plexus for therapy of neurogenic bladder dysfunctions after failure of percutaneous sacral nerve stimulation.* (*Neuromodulation* 13: 141-144—Possover M, Schurch, Henle K P (2010). *New pelvic nerve stimulation strategy for recovery of bladder functions and locomotion in complete paraplegics. Neurourology and Urodynamics* Published Online June 29)

Implantation of electrodes on the femoral nerve and the sacral plexus of the sciatic nerve permits application of electricity to all pelvic and lower extremity nerves. The primary aim of the invention in this case was to permit patients to recover of pelvic functions and/or deambulation. Control over the bladder hyperactivity and spasms in the lower limbs are then based on the low frequency continuous stimulation to the pelvic somatetic nerves. Electrical stimulation is a well-known technique for axon regeneration in peripheral neurosurgery. Histological analysis and measurement of regeneration showed that low stimulation had a more successful outcome than high frequency stimulation on regeneration of damaged sciatic nerves (Lu M C, Ho C Y. Hsu S F, Lee H C, Lin J H, Yao C H, Chen Y S. *Effects of electrical stimulation at different frequencies on regeneration of transacted peripheral nerve. Neuro-rehabilitation and neural repair* 2008; 22: 367-373).

Similarly, for the patients discussed herein, a low frequency current was applied to the sciatic and femoral nerve in order to control spasticity in the lower extremities and bladder hyperactivity. It was observed that pelvic nerve stimulation plays a role in recovery functions. If pelvic nerve stimulation induces axon regeneration, new synapsis connections or just providing the essentially needed directional cue to the sprouting axons, enabling them to properly grow and reconnect with distal corresponding nerves is unknown. This evolution was completely unexpected. Further, it should be noted that both patients were in a long time chronic phase without any improvement. After the inventive procedures, the patients had recovered not just control over "spasticity", function or motion devoid of any functionality in normal life, but had recovered harmonic, voluntaric, controllable and useful functions. With these patients, bladder functions were recovered.

To eventually improve control and harmony of connections, according to the inventor, the patient should not simply use the stimulation for training while concentrating on something else, but to think about his movements during training. Rather, it is believed that mental concentration of the patient helps information coming from the CNS to the level of spinal cord injury, combined with pelvic nerve stimulation from the lower level, create better conditions for re-establishing connection past the point of the injury.

It is clear that these findings are only the beginning of what can be studied much further in clinical observations. Our findings nevertheless lead us to conclude that there is a clear connection between the electrostimulation and guided thoughts of a patient during treatment.

Continuous low frequency stimulation of implanted nerves outside periods of training may be advantageous for control of bladder hyperactivity, and also for reduction of spasticity. Because there is evidence of the role of the sympathetic innervations of bone tissue and its role in the regulation of bone remodelling in humans, and because changes in the autonomic nervous system are believed to cause attrition of SCI bone via changes in vascular tone and flow, it is believed that there is a possible impact of continuous low frequency stimulation on sympathetic fibers contained in the sciatic and the femoral nerves and on bone stability. We also believe there is a possible effect of stimulation on prevention of decubitus lesions. Indeed, not only spinal cord stimulation has been reported in treatment of arteritis of the legs, but also in vivo studies involving animal models have revealed that electric stimulation of wound healing processes results in more collagen deposition, enhanced angiogenesis, greater wound tensile strength, and a faster wound contraction rate. In addition to these direct cellular actions, electric stimulation has been shown to improve tissue perfusion and reduce edema formation that results in a significant increase in transcutaneous oxygen pressures. Therefore, according to the invention, the LION procedure to the pelvic nerves is potentially useful in the rehabilitation of spinal cord injured people and may reduce risks for complications.

The invention claimed is:

1. A method for treating an impaired body function in a patient, comprising the steps of:
    (a) laparoscopically implanting at least one neuroprothesis electrode on at least one endopelvic nerve root of a patient;
    (b) electrostimulating the nerve root with the electrode for a predetermined time period to induce a body function of the patient; and (c) during the predetermined time period, instructing the patient to mentally concentrate on performing the body function, wherein the implanting step comprises identifying a nerve root corresponding to an impaired body function of the patient, and implanting the electrode on the identified nerve root, and wherein the identified nerve root has lost communication with the patient's brain, wherein steps (b) and (c) re-establish communication between the identified nerve root and the patient's brain.

2. The method of claim 1, wherein the body function is selected from the group consisting of leg mobility, sexual function, bladder function, sensation, equilibrium and combinations thereof.

3. The method of claim 1, further comprising the step of using a low frequency charge modulation for the electrostimulating step when the patient is a comatose patient further the low frequency charge modulation has a frequency of up to 10 Hz.

4. The method of claim 1, further comprising the step of using a high frequency charge modulation for the electrostimulating step when the body function involves muscle movement, wherein the high frequency charge modulation has a frequency of at least 10 kHz.

5. The method of claim 1, wherein step (c) further comprises providing the patient with visual indicators related to the body function.

6. The method of claim 1, wherein the at least one endopelvic nerve comprises the femoral nerve.

7. The method of claim 1, wherein the at least one endopelvic nerve comprises the iliac nerve.

\* \* \* \* \*